US008254720B2

(12) United States Patent
Matsuzaki

(10) Patent No.: US 8,254,720 B2
(45) Date of Patent: Aug. 28, 2012

(54) IMAGE EXTRACTING APPARATUS, COMPUTER PROGRAM PRODUCT, AND IMAGE EXTRACTING METHOD

(75) Inventor: Hiroshi Matsuzaki, Tachikawa (JP)

(73) Assignee: Olympus Corporation, Tokyo (JP)

( * ) Notice: Subject to any disclaimer, the term of this patent is extended or adjusted under 35 U.S.C. 154(b) by 1069 days.

(21) Appl. No.: 12/172,616

(22) Filed: Jul. 14, 2008

(65) Prior Publication Data

US 2009/0022400 A1 Jan. 22, 2009

(30) Foreign Application Priority Data

Jul. 20, 2007 (JP) ................................ 2007-190072

(51) Int. Cl.
*G06K 9/36* (2006.01)
(52) U.S. Cl. ........................................ 382/276; 348/700
(58) Field of Classification Search .................... 348/45, 348/65, 72, 135–142, 650, 700, E3.032, E5.067; 382/276; 386/241; 396/17; 600/101, 117, 600/118, 920; D24/138
See application file for complete search history.

(56) References Cited

U.S. PATENT DOCUMENTS

| | | | | |
|---|---|---|---|---|
| 5,694,533 A * | 12/1997 | Richards et al. | ............... | 345/420 |
| 2002/0051077 A1 * | 5/2002 | Liou et al. | ..................... | 348/465 |
| 2002/0186958 A1 * | 12/2002 | Ikeda et al. | ..................... | 386/69 |
| 2006/0210147 A1 * | 9/2006 | Sakaguchi | ..................... | 382/154 |
| 2007/0258698 A1 * | 11/2007 | Okada et al. | ..................... | 386/95 |
| 2008/0181507 A1 * | 7/2008 | Gope et al. | ..................... | 382/190 |
| 2009/0034937 A1 * | 2/2009 | Kusunoki et al. | ............... | 386/96 |
| 2009/0062684 A1 * | 3/2009 | Gregersen et al. | ............ | 600/547 |
| 2010/0194893 A1 * | 8/2010 | Graeser et al. | ................ | 348/159 |

FOREIGN PATENT DOCUMENTS

| | | |
|---|---|---|
| JP | 9-93527 | 4/1997 |
| JP | 2001-54055 | 2/2001 |
| JP | 2006-61626 | 3/2006 |
| JP | 2006-154309 | 6/2006 |
| JP | 2006-217045 | 8/2006 |
| JP | 2006-217046 | 8/2006 |
| JP | 2006-280792 | 10/2006 |
| JP | 2007-75163 | 3/2007 |
| JP | 2007-166090 | 6/2007 |

OTHER PUBLICATIONS

English language computer translation only of Japanese Patent Application Laid-Open No. 2006-217046, Sep. 16, 2008.

* cited by examiner

*Primary Examiner* — Gregory F Cunningham
(74) *Attorney, Agent, or Firm* — Scully, Scott, Murphy & Presser, P.C.

(57) ABSTRACT

Provided are a scene-transition-image extraction unit that extracts a scene transition image from a sequence of successive images using a predetermined extraction condition, a display unit that displays a near image of the scene transition image, an operation history acquiring unit that acquires image information of an image, for which a predetermined viewing operation is performed, among the near image(s) and history information of the operation, an extraction condition changing unit that changes the extraction condition using the image information and the history information of the operation acquired by the operation history acquiring unit. The scene-transition-image extraction unit re-extracts a scene transition image using the extraction condition changed by the extraction condition changing unit.

16 Claims, 12 Drawing Sheets

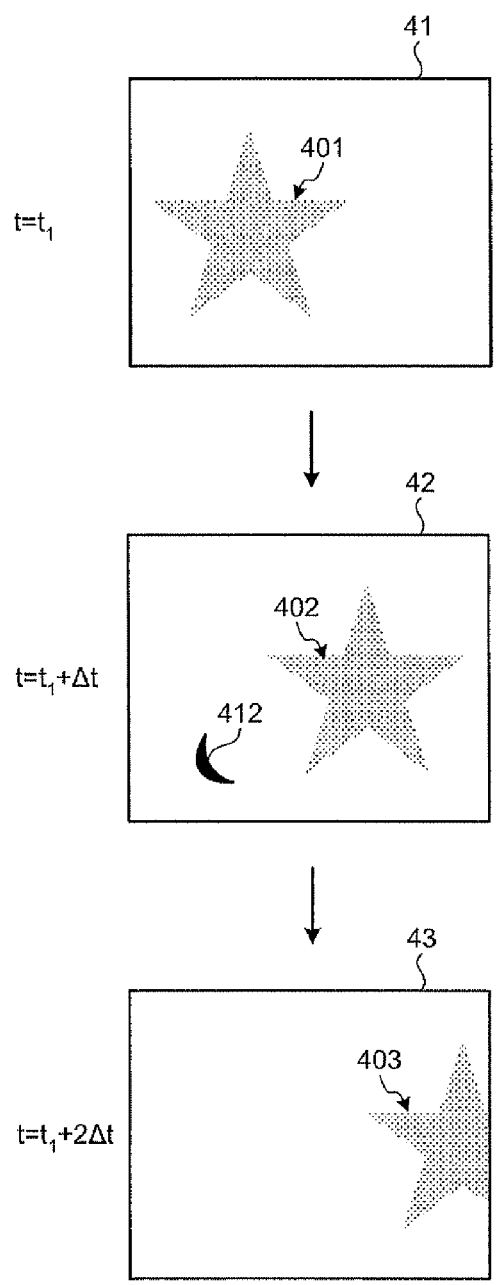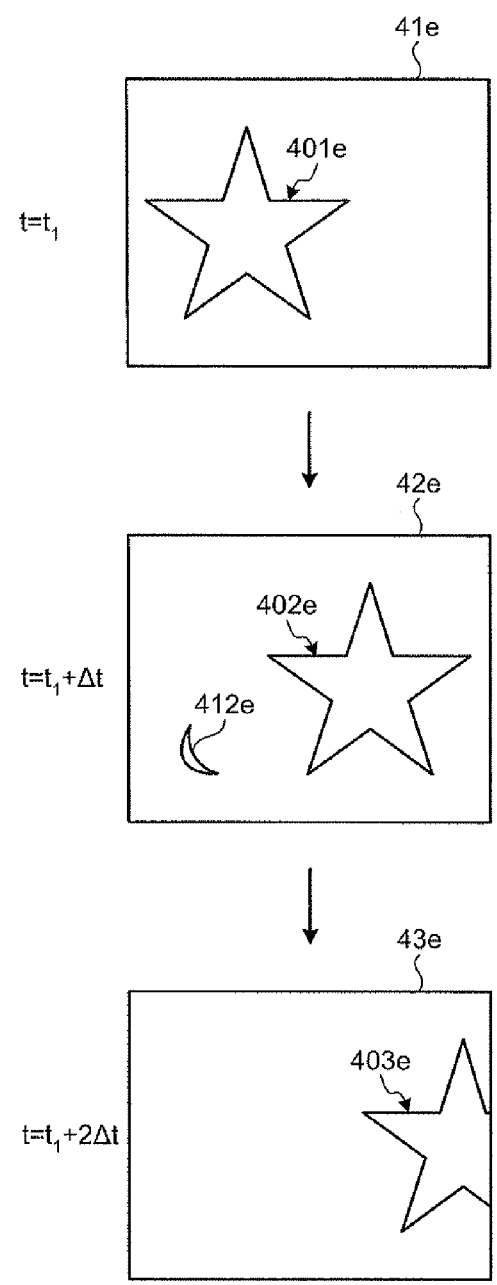

IMAGE EXTRACTING APPARATUS, COMPUTER PROGRAM PRODUCT, AND IMAGE EXTRACTING METHOD

CROSS-REFERENCE TO RELATED APPLICATIONS

This application is based upon and claims the benefit of priority from Japanese Patent Application No. 2007-190072, filed Jul. 20, 2007, the entire contents of which are incorporated herein by reference.

BACKGROUND OF THE INVENTION

1. Field of the Invention

The present invention relates to an image extracting apparatus which extracts a sequence of images serially captured, a point where a scene transition occurs in an image sequence of dynamic image frames, a valid image, and the like, an image extraction program which can be provided as a computer program product, and an image extracting method.

2. Description of the Related Art

Conventionally, there has been known an image extracting apparatus which extracts an image where a scene transition occurs in an image sequence of dynamic images or the like (the image is referred below as "scene transition image"). With the image extracting apparatus, a user checks a predetermined number of extracted scene transition images. The user can roughly understand general contents of the entire image sequence in a short time without checking all images in the image sequence, and can easily identify a desired scene or a desired image (see Japanese Patent Application Laid-Open No. 2001-54055).

Further, according to another conventionally known image extracting apparatus, key frames are extracted as images indicating the contents of a scene from a group of images arranged between scene transition frames in a sequence of dynamic images. Then, an extraction condition for extracting the key frames is changed based on image information of images selected by the user, and key frames are re-extracted (Japanese Patent Application Laid-Open No. 2006-217045, Japanese Patent Application Laid-Open No. 2006-217046).

SUMMARY OF THE INVENTION

An image extracting apparatus according to one aspect of the present invention includes a scene-transition-image extraction unit that extracts as a scene transition image an image where a transition of scene occurs from an image sequence captured in time series, using a predetermined extraction condition, a display unit that displays a near image, which is an image captured at a time in a neighborhood of a time when the scene transition image is captured, an operation history acquiring unit that acquires image information of an image, for which a predetermined viewing operation is performed, among the near image(s) and history information of the predetermined viewing operation, and a changing unit that changes the extraction condition using the image information and the history information of the operation acquired by the operation history acquiring unit. The scene-transition-image extraction unit re-extracts an image where a transition of scene occurs, using the extraction condition changed by the changing unit.

Further, a computer program product according to another aspect of the present invention has a computer readable medium including programmed instructions, and the instructions, when executed by a computer, cause the computer perform extracting as a scene transition image an image where a transition of scene occurs from an image sequence captured in time series, using a predetermined extraction condition, displaying a near image, which is an image captured at a time in a neighborhood of time when the scene transition image is captured, acquiring image information of an image, for which a predetermined viewing operation is performed, among the near image(s) and history information of the predetermined viewing operation, changing the extraction condition using the image information and the history information of the operation acquired, and re-extracting an image where a transition of scene occurs using the extraction condition changed.

Further, an image extracting method according to still another aspect of the present invention includes extracting as a scene transition image an image where a transition of scene occurs from an image sequence captured in time series, using a predetermined extraction condition, displaying a near image, which is an image captured at a time in a neighborhood of time when the scene transition image is captured, acquiring image information of an image, for which a predetermined viewing operation is performed, among the near image(s) and history information of the predetermined viewing operation, and changing the extraction condition using the image information and the history information of the operation acquired in the acquiring, wherein in the extracting, an image where a transition of scene occurs is re-extracted according to the extraction condition changed in the changing.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 5 is a diagram of a specific example of images in an image sequence;

FIG. 6 is a diagram of edge extraction images acquired through an edge extraction process performed on the images shown in FIG. 5;

DETAILED DESCRIPTION OF THE PREFERRED EMBODIMENTS

Figure 1:
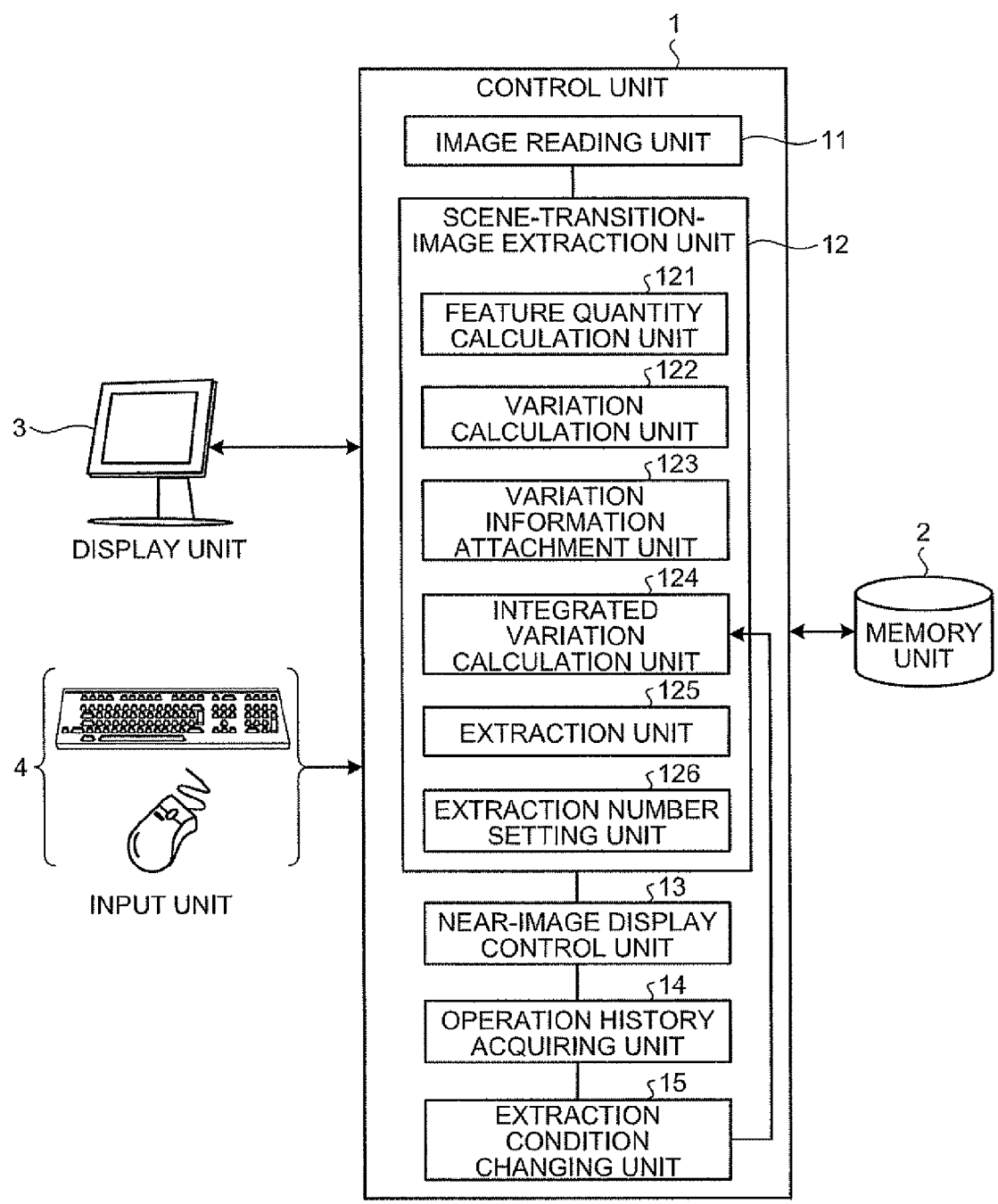
FIG. 1 is a block diagram of a configuration of an image extracting apparatus according to an embodiment of the present invention.

Exemplary embodiments of an image extracting apparatus, an image extraction program, and an image extracting method according to the present invention are described below with reference to accompanying drawings. Here, the present invention is not limited to the embodiments. In the description of the drawings, a same reference character is attached to a same element or a corresponding element.

FIG. 1 is a block diagram of a configuration of an image extracting apparatus according to an embodiment of the present invention. The image extracting apparatus shown in FIG. 1 includes a control unit 1 that has an operation function and a control function, a memory unit 2 that stores various kinds of information including image information of an image sequence, a display unit 3 that outputs and displays information including an image, and an input unit 4 such as a keyboard and a mouse. The image extracting apparatus is realized with a computer having a central processing unit (CPU), a read-only memory (ROM), a random access memory (RAM), and the like.

The control unit 1 has an image reading unit 11 that reads in images which are sequential in time series as an image sequence and are stored in the memory unit 2. Further, the control unit 1 has a scene-transition-image extraction unit 12 and a near-image display control unit 13. The scene-transition-image extraction unit 12 extracts a scene transition image from the images in the image sequence that is read in by the image reading unit 11, using a predetermined extraction condition. Further, the near-image display control unit 13 controls the display unit 3 to display a near image captured at a time point in the neighborhood of time point at which the scene transition image extracted by the scene-transition-image extraction unit 12 is captured.

Further, the control unit 1 has an operation history acquiring unit 14 and an extraction condition changing unit 15. The operation history acquiring unit 14 acquires image information of a near image, for which the user performs a predetermined viewing operation, among the near images displayed on the display unit 3, and history information of the operation indicating contents of the operation. The extraction condition changing unit 15 changes the extraction condition for extracting the scene transition image using the image information and the history information of the operation acquired by the operation history acquiring unit 14. Here, in the present embodiment, the operation history acquiring unit 14 further acquires image information and history information of an operation of a scene transition image for which the user performs a predetermined viewing operation. Then, in changing the extraction condition, the extraction condition changing unit 15 uses the information of the scene transition image acquired by the operation history acquiring unit 14 in addition to the information of the near image.

The scene-transition-image extraction unit 12 has a feature quantity calculation unit 121, a variation calculation unit 122, a variation information attachment unit 123, an integrated variation calculation unit 124, an extraction unit 125, and an extraction number setting unit 126. The feature quantity calculation unit 121 calculates a plurality of predetermined feature quantities for each image that is read in by the image reading unit 11. The variation calculation unit 122 calculates a variation of a feature quantity, which is calculated by the feature quantity calculation unit 121, between predetermined images. The variation information attachment unit 123 attaches information on feature quantity variation calculated by the variation calculation unit 122 to a corresponding image. Further, the integrated variation calculation unit 124 calculates an integrated variation, which is a combination and integration of feature quantity variations of each image, using the information of feature quantity variations attached to each image. Further, the extraction unit 125 extracts a number of images from the image sequence using the integrated variation calculated by the integrated variation calculation unit 124 for each image. The number is set beforehand by the extraction number setting unit 126. Here, the number of images to be extracted (i.e., extraction number) is set beforehand by the extraction number setting unit 126. Alternatively, the user may input the extraction number to the extraction number setting unit 126 via the input unit 4.

A CPU of the image extracting apparatus having each of the units described above reads out an image extraction program for performing an image extraction process according to the present embodiment from the memory unit 2, and performs an operation process related to the image extraction process. Further, the image extraction program according to the present embodiment may be recorded in a computer-readable recording medium such as a flexible disk, a CD-ROM, a DVD-ROM, and a flash memory, so as to be widely distributed. Therefore, the image extracting apparatus may include an auxiliary memory device that can perform reading of one of the various kinds of recording mediums listed above.

Figure 2:
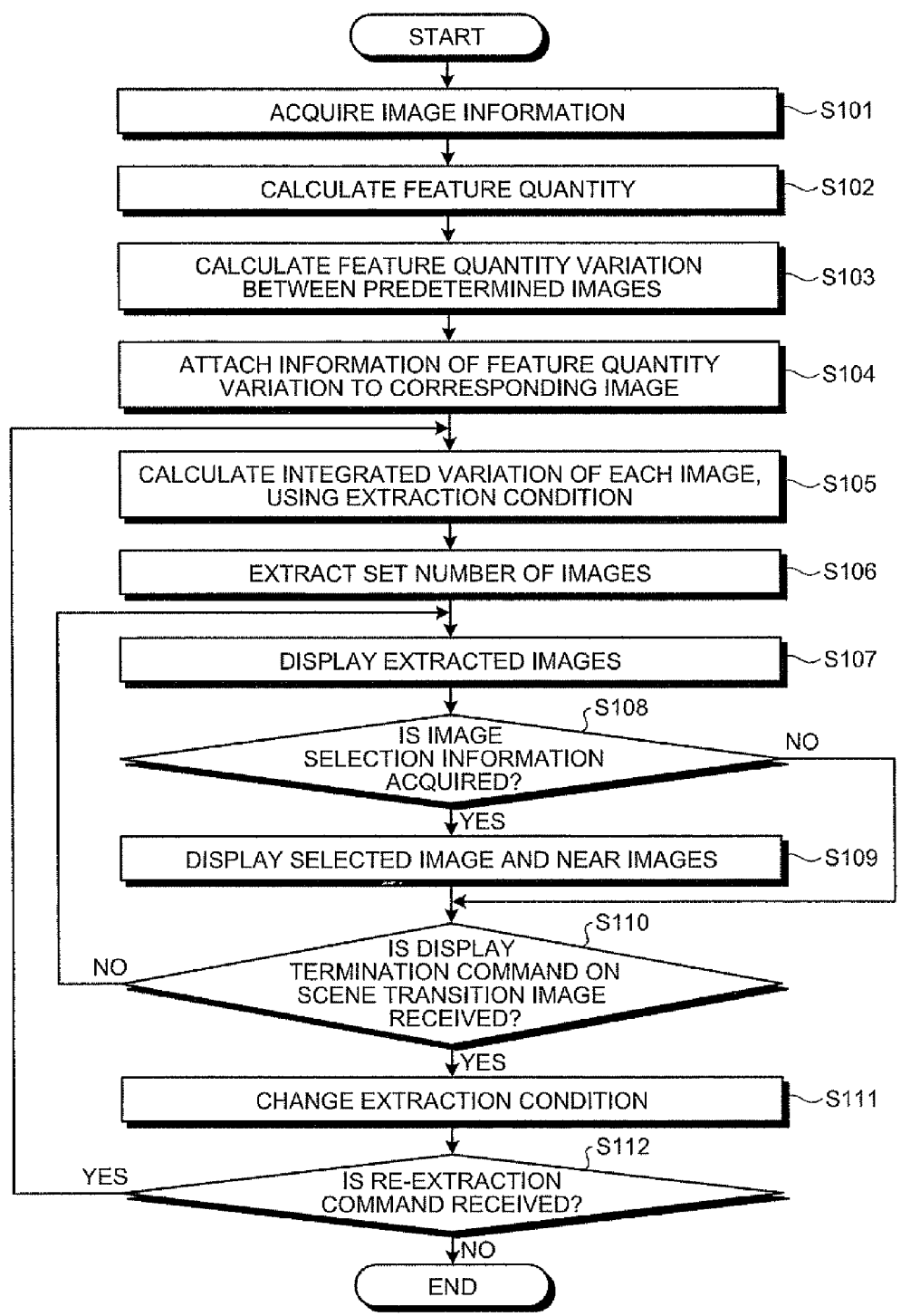
FIG. 2 is a flowchart of an image extraction process and an extraction condition change process performed by the image extracting apparatus shown in FIG. 1.

FIG. 2 is a flowchart of an image extraction process procedure according to the present embodiment. Firstly, the image reading unit 11 reads in information such as a total number of images forming an image sequence and a size of an image from the memory unit 2 (Step S101). Then, the feature quantity calculation unit 121 calculates the feature quantity of each image using the image information read in by the image reading unit 11 (Step S102). Here, plural feature quantities are calculated for one image. Then, the variation calculation unit 122 calculates the feature quantity variation between images separate from each other by a predetermined time interval (Step S103). Here, the variation calculation unit 122 calculates a variation of each of the feature quantities. The variation information attachment unit 123 attaches information of the feature quantity variations calculated by the variation calculation unit 122 to a corresponding image (Step S104).

Next, the integrated variation calculation unit 124 calculates the integrated variation, which is a unique amount for each image, using the feature quantity variations attached to each image (Step S105). For example, the integrated variation calculation unit 124 calculates the integrated variation by weighting each feature quantity variation using a weighting factor set for each feature quantity, and integrating the weighted feature quantity variations. In the present embodiment, the weighting factor of each feature quantity is set as an extraction condition of the scene transition image.

Then, the extraction unit 125 extracts a number of images from the image sequence in descending order of integrated variation as the scene transition image (Step S106). The number is set by the extraction number setting unit 126. Further, the scene-transition-image extraction unit 12 outputs the scene transition images extracted by the extraction unit 125 and displays the scene transition images on the display unit 3 (Step S107).

Then, the control unit 1 determines whether the user selects any of the scene transition images displayed on the display unit 3 via the input unit 4 (Step S108). If image selection information indicating that an image is selected is acquired (Step S108: Yes), the near image display control unit 13 displays the selected scene transition image and near images of the selected scene transition image on the display unit 3 (Step S109). On the other hand, if the image selection information is not acquired (Step S108: No), the control unit 1 proceeds to step S110. Alternatively, near images may be displayed regardless of the selection of the scene transition image.

At step S110, the control unit 1 determines whether a display termination command on the scene transition image is acquired. If the display termination command on the scene transition image is not acquired (Step S110: No), the control unit 1 proceeds to step S107 and repeats the procedures described above. On the other hand, if the display termination command on the scene transition image is acquired (Step S110: Yes), the extraction condition changing unit 15 changes the extraction condition and stores the extraction condition in the memory unit 2 (Step S111). To be specific, the extraction condition changing unit 15 changes the weighting factor, which is an extraction condition, of each feature quantity using information acquired by the operation history acquiring unit 14 before the termination command is acquired, more specifically, using the image information of the image, for which the user performs the predetermined viewing operation, among the scene transition image and the near images displayed on the display unit 3 and the history information of the operation. On the other hand, if the display termination command on the scene transition image is not acquired (Step S110: No), the control unit 1 proceeds to step S107 and repeats the procedures described above.

Next, the control unit 1 determines whether or not a re-extraction command on the scene transition image is input to the scene-transition-image extraction unit 12 (Step S112). If the re-extraction command on the scene transition image is input (Step S112: Yes), the control unit 1 proceeds to Step S105, where the integrated variation calculation unit 124 calculates the integrated variation of each image again using the changed weighting factor, and repeats the procedures at step S106 and subsequent steps. On the other hand, if the re-extraction command on the scene transition image is not input to the scene-transition-image extraction unit 12 (Step S112: No), the control unit 1 terminates the image extraction process.

Here, an image for which the user performs the predetermined viewing operation includes images for which the user performs a selection operation, and images for which an operation indicating that the image is not a key image is performed. An image for which an operation indicating that the image is not a key image is performed is, for example, an image for which a deletion operation is performed, and an image for which a jump operation such as a skip is performed while the images are sequentially displayed in order of time series, i.e., while the images are displayed as a movie. In short, those are images for which the user does not perform the viewing operation on purpose.

The image extracting apparatus extracts the scene transition image and the near image in the neighborhood of the scene transition image in the image extraction process shown in FIG. 2, and displays the extracted images on the display unit 3. The image extracting apparatus changes the extraction condition using the image information of an image for which the user performs a viewing operation and a predetermined operation, among the scene transition image and the near image, and the history information of the operation, and then re-extracts the scene transition image using the changed extraction condition.

Figure 3:
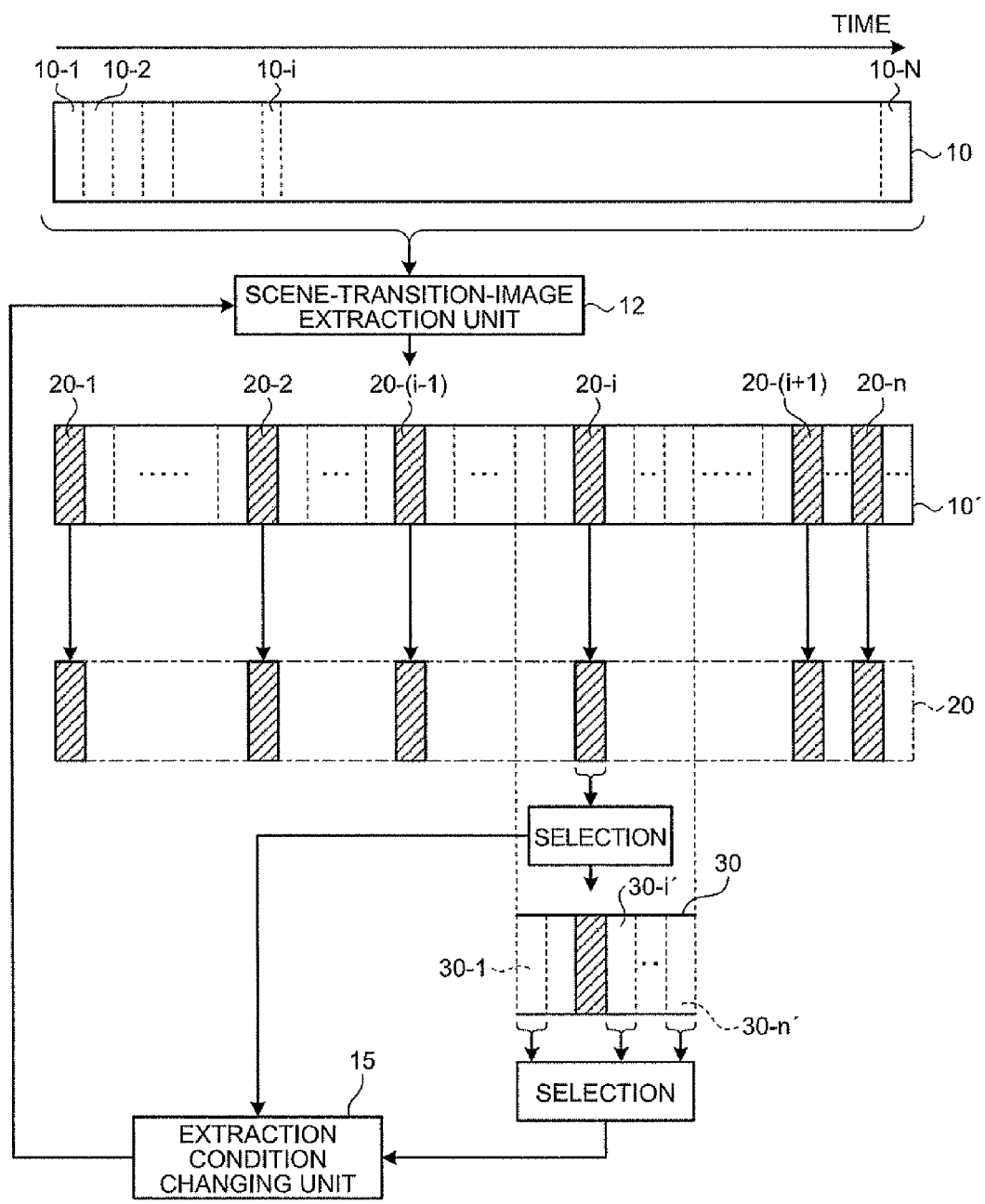
FIG. 3 is a schematic diagram of the image extraction process and the extraction condition change process performed by the image extracting apparatus shown in FIG. 1.

Now, a specific image extraction process according to the image extraction process described above is described in detail with reference to FIG. 3. FIG. 3 is a schematic diagram of a process to extract an image from an image sequence containing sequential images arranged in time series, using a predetermined extraction condition, and to change the extraction condition using image information of an image for which the predetermined viewing operation is performed, among the extracted images, and history information of the operation. An image sequence 10, which contains sequential images arranged in time series, has N images 10-1 to 10-N arranged at time interval $\Delta t$ to each adjacent image. In the processes at step S102 to step S106 shown in FIG. 2, a scene transition image sequence 20 containing n (n<N) pieces of scene transition images 20-1 to 20-n are extracted from the image sequence 10. As a result, the images 10-1 to 10-N are divided into n portions by the scene transition images 20-1 to 20-n. Then, in the process at step S107, the scene transition images 20-1 to 20-n are displayed on the display unit 3.

When the user performs the selection operation on the scene transition image 20-i in the scene transition images 20-1 to 20-n as displayed, the scene transition image 20-i and a near image sequence 30 including near images 30-1 to 30-n' of the scene transition image 20-i, are displayed on the display unit 3 by the process at step S109. Here, a value of n' may be specified by the user or may be set as a predetermined value. Alternatively, the value may be set corresponding to the number of images between the scene transition image 20-(i−1) and the scene transition image 20-i or the number of images between the scene transition image 20-i and the scene transition image 20-(i+1). In the example shown in FIG. 3, the near images 30-1 to 30-n' are n' images among images previous to or subsequent to the scene transition image. Not limited to the example shown in FIG. 3, n' images previous to the scene transition image 20-i may be displayed as the near images, or n' images subsequent to the scene transition image 20-i may be displayed as the near images.

Further, in the process at step S111, the extraction condition is changed based on the image information of the image for which the user performs the predetermined viewing operation such as the selection operation, for example, based on the image information of the scene transition image 20-i and the near image 30-i' shown in FIG. 3, and the history information of the operation.

Figure 4:
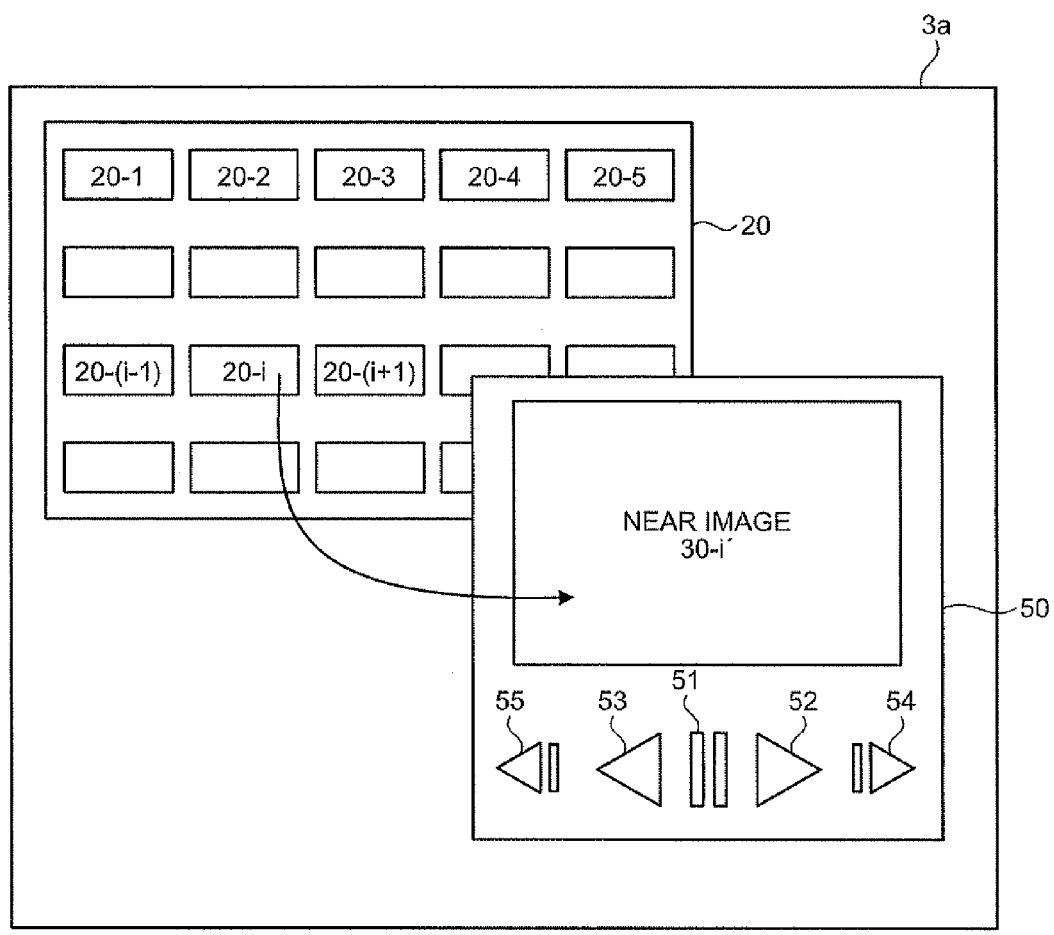
FIG. 4 is a diagram of a display example of an image that is extracted by the image extracting apparatus shown in FIG. 1.

FIG. 4 is a diagram of a display example of the scene transition images and the near images. As shown in FIG. 4, the scene transition images 20-1 to 20-n are displayed as thumbnails on a display screen 3a of the display unit 3. Further, as shown in FIG. 4, when the user performs the selection operation on the scene transition image 20-i, the near image sequence containing the near images 30-1 to 30-n' is displayed as a movie on a movie display area 50. The movie display area 50 has a pause button 51, a play button 52, a reverse play button 53, a frame advance forward button 54, and a frame advance backward button 55. The pause button 51 is a button which allows an input of a command to the control unit 1 to pause the displayed movie and keep the displayed movie still until other operation is performed. The play button 52 is a button which allows an input of a command to the control unit 1 to display images sequentially in order of time series, and the reverse play button 53 is a button which allows an input of a command to the control unit 1 to play the images sequentially in reverse order of time series. The frame advance forward button 54 and the frame advance backward button 55 are buttons which allow inputs of a command to the control unit 1 to slow down a play-speed in a corresponding direction, and to lengthen display time of each image. Here, an image for which the user performs the viewing operation and the predetermined operation is an image displayed on the display unit 3 when the button described above is selected by the user.

Next, a specific example of the feature quantity of an image, the scene transition image, and the near image is described with reference to FIGS. 5 and 6. Firstly, FIG. 5 is a diagram of an example of images in the image sequence 10. In FIG. 5, star-shaped objects 401, 402, and 403 appear respectively in three images 41 (time $t=t_1$), 42 (time $t=t_1+\Delta t$), and 43 ($t=t_1+2\Delta t$) which are sequential at time interval $\Delta t$. The three star-shaped objects 401, 402, and 403 are the same object. FIG. 5 illustrates a case where the star-shaped object is in constant motion horizontally rightward within the same visual field. A crescent-shaped object 412 that is smaller than the star-shaped object 402 also appears in the image 42.

The feature quantity of the images shown in FIG. 5 is, for example, a color and a number of pixels of the objects 401, 402, and 403. Further, the feature quantity may be calculated based on an edge extraction image shown in FIG. 6 which is acquired through an edge extraction process (or a contour extraction process) on the objects 401, 402, 403, and 412 in the images 41, 42, and 43 shown in FIG. 5. As shown in FIG. 6, an edge 401e of the object 401 is shown in an edge extraction image 41e. An edge 402e of the object 402 and an edge 412e of the object 412 are shown in an edge extraction image 42e. An edge 403e of the object 403 is shown in an edge extraction image 43e. Now, an area of a portion surrounded by the edge (hereinafter referred to as "area of edge") is set as one feature quantity of the image. The area of the edge 401e which is a feature quantity of the image 41 is the same as the area of the edge 402e which is a feature quantity of the image 42, whereas the area of the edge 403e which is a feature quantity of the image 43 is smaller than the area of the edge 401e or the area of the edge 402e.

Therefore, the variation of the feature quantity between an image and another image at time interval $\Delta t$ is used as the feature quantity variation between predetermined images. When the weighting factor for the area of the edge is high while the weighting factors for other feature quantities are low, the image extracting apparatus extracts the image 43 from the images 41, 42, and 43 as the scene transition image and displays the image 43 on the display unit 3.

The image extracting apparatus according to the embodiment displays the near image of the scene transition image selected by the user. Therefore, when the user selects the image 43, the image extracting apparatus displays a predetermined number of near images including the image 42 on the display unit 3. Here, if an image in which the crescent-shaped object 412 appears is an image the user desires as the scene transition image, the user may perform the predetermined viewing operation such as the selection operation on the image 42. When the viewing operation is performed, the image extracting apparatus according to the embodiment changes the extraction condition, using the image information of the image 42. As a result, the extraction condition is changed so that an image in which the crescent-shaped object 412 appears is more likely to be extracted as the scene transition image in subsequent extraction of the scene transition image. For example, the image extracting device according to the embodiment changes the extraction condition so as to increase the weighting factor of the variation of the feature quantity such as a color and a shape of an object.

Alternatively, in the present embodiment, a quantity other than the feature quantities described above may be used as the feature quantity variation of an image. For example, normalized cross-correlation may be used as the feature quantity variation, and also a degree of similarity such as SSD (sum of squared differences between corresponding pixels), and SAD (sum of absolute values of differences between corresponding pixels) may be used as the feature quantity variation. Further, SSD or SAD of results acquired by multiplication or division of average pixel value of all images in the image sequence may be used as the feature quantity variation. Further, SSD or SAD of results acquired by multiplication or division of average pixel value of each image acquired by dividing an image may be used as the feature quantity variation. Further, it is possible to calculate a point selected regularly within a space (e.g. selected at regular intervals) or a feature point where a feature locally stands out, and use an amount of movement of such point or the size of optical flow (absolute value) of such point as the feature quantity variation. The feature quantity variations mentioned above are qualitatively different from the variation calculated based on the area surrounded by the edge as the feature quantity. When the various types of feature quantity variations are integrated and employed as the integrated variation, an image can be extracted from various points where the scene undergoes transition in various different manners.

Now, a process to change the extraction condition is described specifically. Firstly, a process to extract the scene transition image using the feature quantity variations attached to each image, and to further extract the near images of the scene transition image is described. In the description below, M (M is an integer larger than or equal to 2) is a number of feature quantities of an image in the image sequence 10, and N (N is an integer larger than or equal to 2) is a number of images in the image sequence 10. Further, image information of the images 10-1 to 10-N in the image sequence 10 is set as $I_1$ to $I_N$ sequentially in order of time the images are captured. The feature quantity variations attached to the images in the image sequence 10 can be represented by a variation matrix $\Delta F$ of following formula (1), where $\Delta F_{qp}$ represents a p-th feature quantity that is attached to a q-th image by the variation information attachment unit 123.

$$\Delta F = \begin{bmatrix} \Delta F_{11} & \Delta F_{12} & \ldots & \Delta F_{1p} & \ldots & \Delta F_{1M} \\ & \Delta F_{22} & & \vdots & & \vdots \\ \vdots & & \ddots & & & \\ \Delta F_{q1} & \ldots & & \Delta F_{qp} & & \\ \vdots & & & & \ddots & \\ \Delta F_{N1} & & & & & \Delta F_{NM} \end{bmatrix} \quad (1)$$

In the embodiment, various kinds of feature quantities are used and the size of each feature quantity is not standardized. Therefore, if a vector consists simply of variations of respective feature quantities as its components, when a threshold process is performed on the size of the vector, an influence of a feature quantity with relatively high value becomes dominant and an influence of a feature quantity with relatively low value is not reflected. Hence, in the embodiment of the present invention, a normalization process is performed on the feature quantity variations calculated by the variation calculation unit 122, and values obtained through the normalization process are employed as components of a vector of the feature quantity variations. The vector thus obtained is employed as a variation vector of each image.

To be specific, variation vector $\vec{f}_q$ of an image 10-$q$ is expressed by following formula (2).

$$\vec{f}_q = \sum_{j=1}^{M} W_j \{\kappa_j \cdot (\Delta F_{qj} - \Delta \overline{F}_j) \} \cdot \vec{i}_q \qquad (2)$$

In the formula, unit vector $\vec{i}_q$ (p=1, 2, ..., M) of dimensions corresponding to respective feature-quantity directions satisfies $\forall p, p', i_p \perp i_{p'} (p \neq p', p=1, 2, ..., M)$. Further, $W_1$ to $W_M$ are weighting factors different for each feature quantity.

An average of the feature quantities of the image $\Delta \overline{F}_p$ and a normalization coefficient $\kappa p$ are expressed in following formulas (3) and (4).

$$\Delta \overline{F}_j = \frac{1}{N} \sum_{j=1}^{N} \Delta F_{qj} \qquad (3)$$

$$\kappa_j = \left\{ \frac{1}{N} \sum_{j=1}^{N} (\Delta F_{ip} - \Delta \overline{F}_p)^2 \right\}^{-\frac{1}{2}} = \frac{1}{\sigma_p} = \frac{1}{\sqrt{v_p}} \qquad (4)$$

In the formula (4), $\sigma_p$ represents standard deviation and $v_p$ represents decentration.

When the variation vector of each image is represented by the formula (2), integrated variation $Sim_q$ which is a combination and integration of feature quantity variations of each image is expressed by following formula (5).

$$Sim_q = |\vec{f}_q| \qquad (5)$$

The integrated variation $Sim_q$ represents a degree of similarity between predetermined images. When $Sim_q$ is low, a degree of similarity between predetermined images is high. Therefore, the extraction unit 125 in the scene-transition-image extraction unit 12 extracts a predetermined number of images in descending order of the integrated variation $Sim_q$ as the scene transition image. The near-image display control unit 13 displays on the display unit 3 a predetermined number of images which are near the scene transition image selected by the user.

Next, a process to change the weighting factor, that is, the extraction condition, using image information of an image for which the user performs the viewing operation and the predetermined operation, among the scene transition images and the near images, and history information of the operation is described specifically. In the present embodiment, relevance feedback, which is a technique used in the field of information retrieval, is used to change the extraction condition. The extraction condition changing unit 15 calculates a weighting factor matrix w' using image information of an image for which the user performs the viewing operation and the predetermined operation, history information of the operation, and formula (6).

$$w' = \alpha w + \beta \sum_{F_i \in D_R} F_i - \gamma \sum_{F_j \in D_R} F_j \qquad (6)$$

In the formula (6), w and w' are matrixes of weighting factors, and are expressed by following formulas (7) and (8).

$$w = (w_1\ w_2\ \ldots\ w_M) \qquad (7)$$

$$w' = (w_1'\ w_2'\ \ldots\ w_M') \qquad (8)$$

Further, $F_i$ and $F_j$ are matrixes representing the variations of feature quantities for each image, and are expressed by following formulas (9) and (10).

$$F_i = (\Delta F_{i1}\ \Delta F_{i2}\ \ldots\ \Delta F_{iM}) \qquad (9)$$

$$F_j = (\Delta F_{j1}\ \Delta F_{j2}\ \ldots\ \Delta F_{jM}) \qquad (10)$$

In the formula (6), $\alpha$, $\beta$, and $\gamma$ are constant numbers larger than or equal to 0. The constant numbers $\alpha$, $\beta$, and $\gamma$ are set based on a relation between the integrated variation $Sim_q$ and the changed weighting factor matrix w'. Here, $D_R$ represents a group of images desired by the user, and $D_N$ represents a group of images not desired by the user. The extraction condition changing unit 15 determines whether an image is desired by the user or not using the history information of the operation. Using the formula (6), the extraction condition changing unit 15 changes the weighting factor so that the feature quantity with a large variation is weighted heavier in an image desired by the user while the feature quantity with a large variation is weighted tighter in an image not desired by the user. Further, as a specific process, the extraction condition changing unit 15 assigns information of changed feature quantity variation matrixes $F_i$ and $F_j$, and the unchanged weighting factor matrix w in the formula (6). Then, the extraction condition changing unit 15 increases/decreases the constant numbers $\alpha$, $\beta$, and $\gamma$ to find the weighting factor matrix w', according to which the integrated variation $Sim_q$ of a predetermined image is lowest. The extraction condition changing unit 15 calculates the integrated variation $Sim_q$ of images other than the predetermined image, using the found weighting factor matrix w'.

As described above, the image extracting apparatus can change the extraction condition of the scene transition image using image information of the scene transition image 20-$i$, which is extracted according to the predetermined extraction condition of the scene transition image, as well as image information of the near image 30-$i'$, which is not extracted according to the predetermined extraction condition. Thus, the image extracting apparatus can change the extraction condition extensively reflecting an intention of the user, for example, by complementing the predetermined extraction condition with a condition which is not included therein. Therefore, the image extracting apparatus according to the embodiment is effective in successfully extracting the scene transition image desired by the user.

Figure 7:
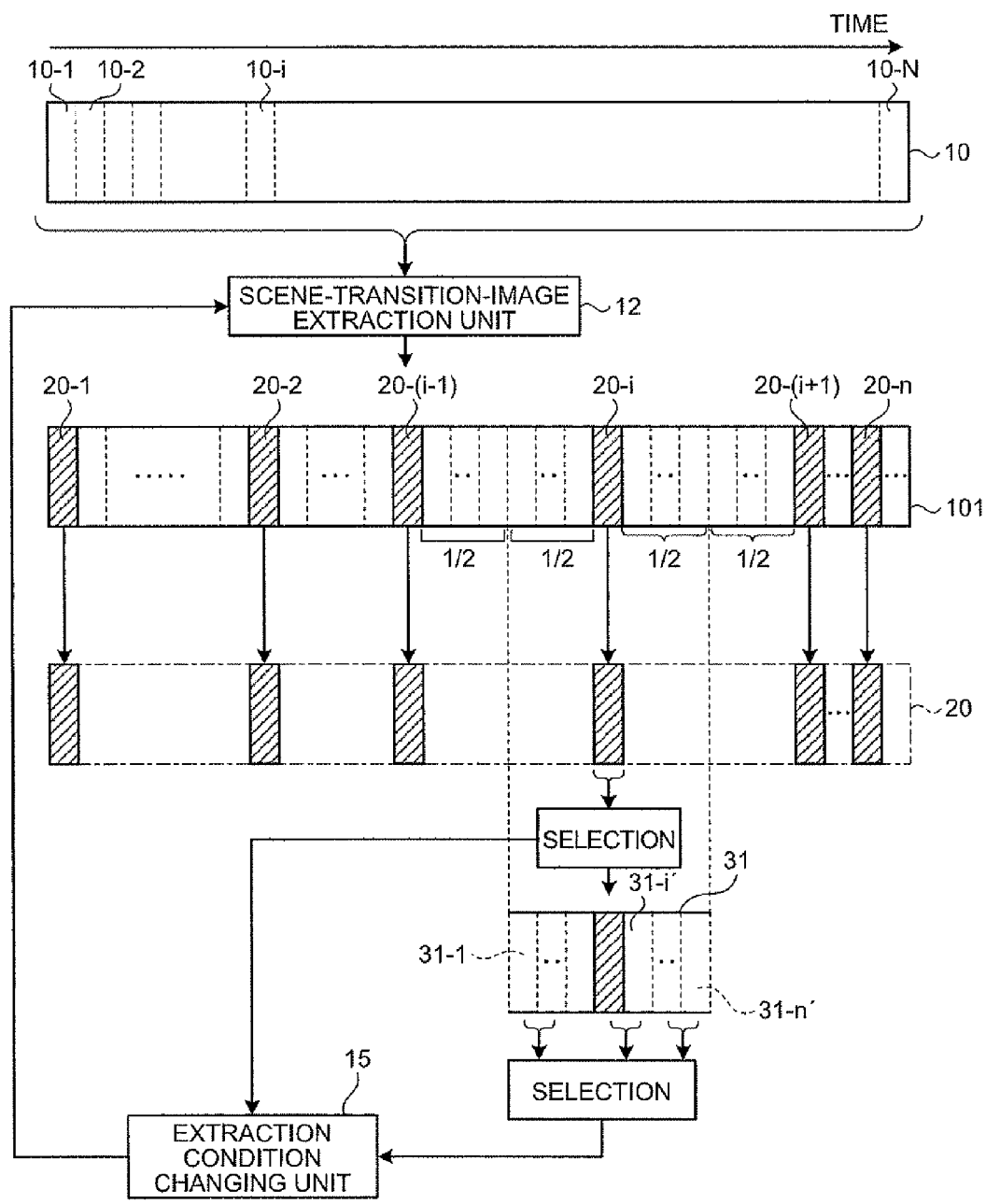
FIG. 7 is a schematic diagram of an image extraction process and an extraction condition change process performed by an image extracting apparatus according to a first modification.

In the embodiment described above, the near image is a number of images near the scene transition image, and the number is set according to the number of images between the scene transition images. In a first modification, at least half of the images between the scene transition images are treated as the near image. For example, as shown in FIG. 7, the near-image display control unit 13 displays on the display unit 3 a near image sequence 31, which contains half a number of images near the scene transition image 20-*i* and captured during a time period between a time when the scene transition image 20-*i* selected by the user is captured and a time when the scene transition image 20-(*i*−1) is captured, and also contains half a number of images near the scene transition image 20-*i* and captured during a time period between the time when the scene transition image 20-*i* selected by the user is captured and a time when the scene transition image 20-(*i*+1) is captured. In other words, the near-image display control unit 13 displays as the near images on the display unit 3 at least half a number of images captured previous to and subsequent to the scene transition image 20-*i* during the time period between the time when the scene transition image 20-*i* is captured and a time when another scene transition image is captured.

In the first modification, each image in the image sequence 10 is either the scene transition image or the near image, and the image extracting apparatus according to the first modification can change the extraction condition using image information of any image in the image sequence 10. Therefore, the image extracting apparatus according to the first modification is effective in more securely extracting the scene transition image desired by the user.

Figure 8:
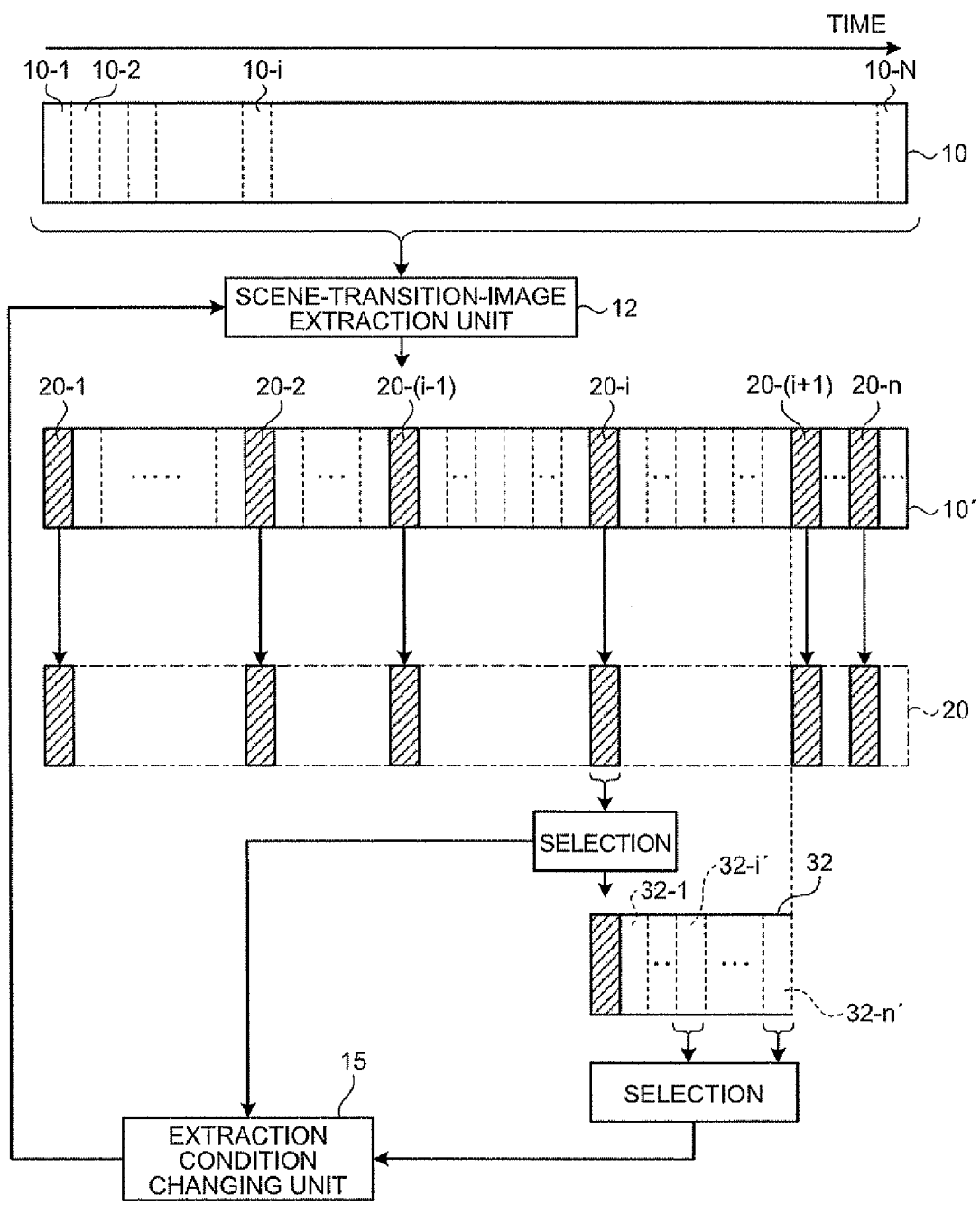
FIG. 8 is a schematic diagram of an image extraction process and an extraction condition change process performed by an image extracting apparatus according to a second modification.

Further, in a second modification, at least all images captured during a time period between a time when the predetermined scene transition image is captured and a time when another scene transition image is captured are displayed as the near images. For example, as shown in FIG. 8, the image extracting apparatus according to the second modification displays all images between the scene transition image 20-*i* selected by the user and the scene transition image 20-(*i*+1), as a near image sequence 32 of the scene transition image 20-*i*.

The image extracting apparatus according to the second modification displays at least all images in a previous scene or a subsequent scene of the scene transition image 20-*i* selected by the user. Therefore, the user can view images scene by scene and grasp a general content of the scene between the scene transition images before changing the extraction condition. In the second modification, the image extracting apparatus may display images, from an image that is one or more images previous to the scene transition image 20-*i* to the scene transition image 20-(*i*+1), as near images. Alternatively, the image extracting apparatus may display all images in a previous scene and a subsequent scene of the scene transition image, that is, all images in two scenes before and after the scene transition image. In the second modification, similarly to the first modification, each image in the image sequence 10 is either the scene transition image or the near image, and the image extracting apparatus can change the extraction condition using image information of any image in the image sequence 10. Therefore, the image extracting apparatus is effective in even more securely extracting the scene transition image desired by the user.

Figure 9:
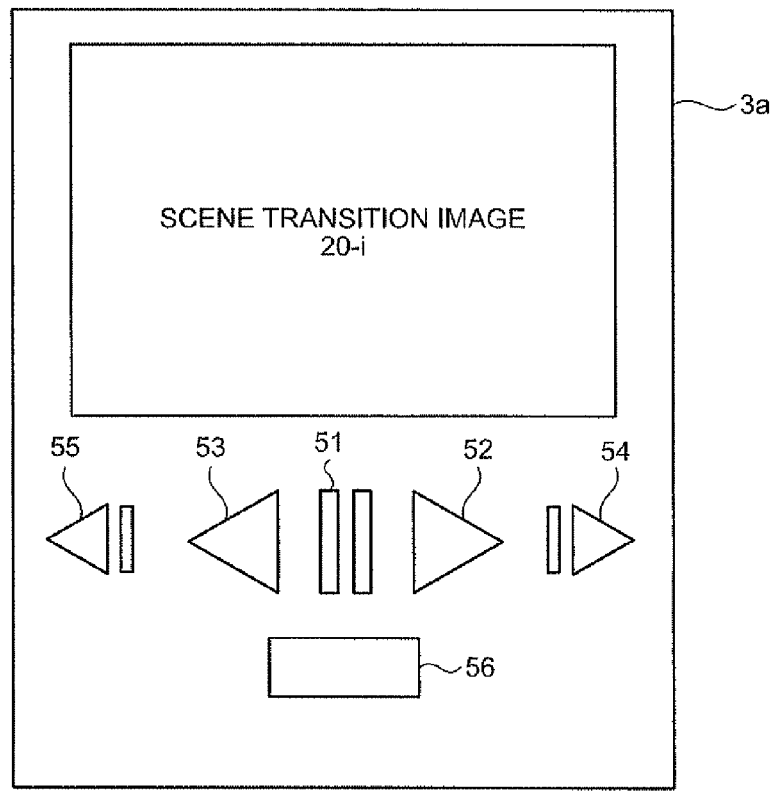
FIG. 9 is a diagram of a display example of an image extracted by the image extracting apparatus shown in FIG. 1.

In the embodiment described above, the image extracting apparatus displays the scene transition images 20-1 to 20-*n* as thumbnails on the display screen 3*a*. An image extracting apparatus according to a third modification displays the scene transition images 20-1 to 20-*n* as a movie on the display screen 3*a*. As shown in FIG. 9, the image extracting apparatus according to the third modification displays the scene transition images 20-1 to 20-*n* in order of time series as a movie. When the user selects the selection button 56, the image extracting apparatus according to the third modification displays as a movie on the display screen 3*a* the near images of the scene transition image 20-*i* that is displayed on the display screen 3*a* when the user selects the selection button 56. The near images displayed are any of the near images described with reference to FIGS. 3, 7, and 8.

The image extracting apparatus according to the third modification displays the scene transition image one by one on the display screen 3*a*, decreasing a risk of user's missing a desired scene transition image by not noticing the image even though the desired image is displayed.

Figure 10:
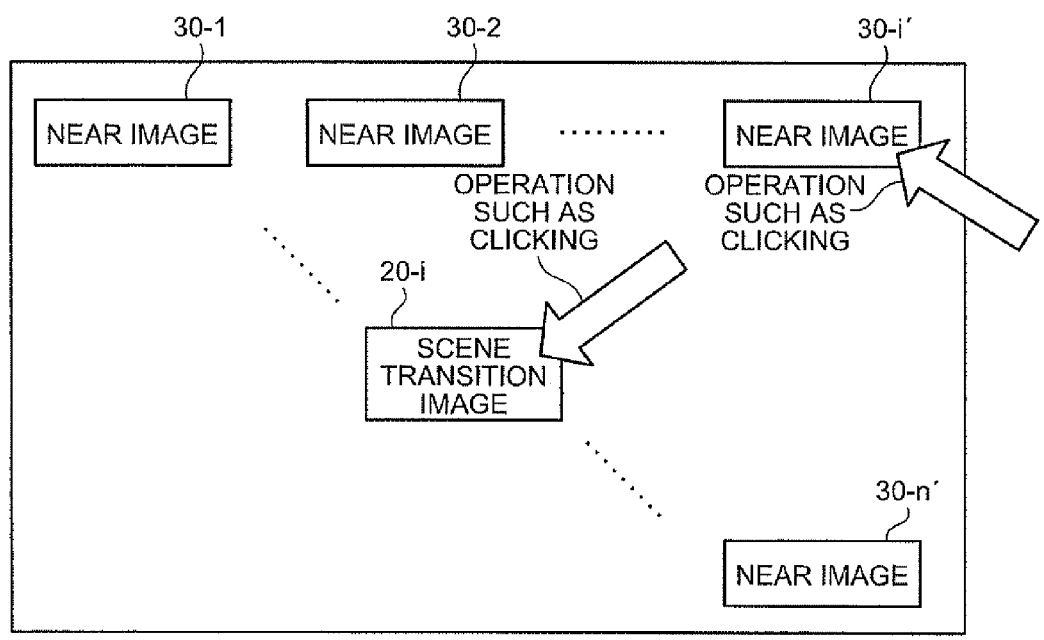
FIG. 10 is a diagram of a display example of images extracted by the image extracting apparatus shown in FIG. 1.

In the embodiment described above, the image extracting apparatus displays the near images 30-1 to 30-*n*' as a movie. An image extracting apparatus according to a fourth modification displays the near images 30-1 to 30-*n*' as thumbnails. As shown in FIG. 10, when the scene transition image 20-*i* is selected, the image extracting apparatus according to the fourth modification displays the scene transition image 20-*i* and the near images 30-1 to 30-*n*' as thumbnails.

As the image extracting apparatus according to the fourth modification displays the scene transition image 20-*i* and the near images 30-1 to 30-*n*' together, the user can view each image in comparison with other images. Therefore, the image extracting apparatus according to the fourth modification allows the user to successfully identify a difference between the near images and to easily find a desired image.

Figure 11:
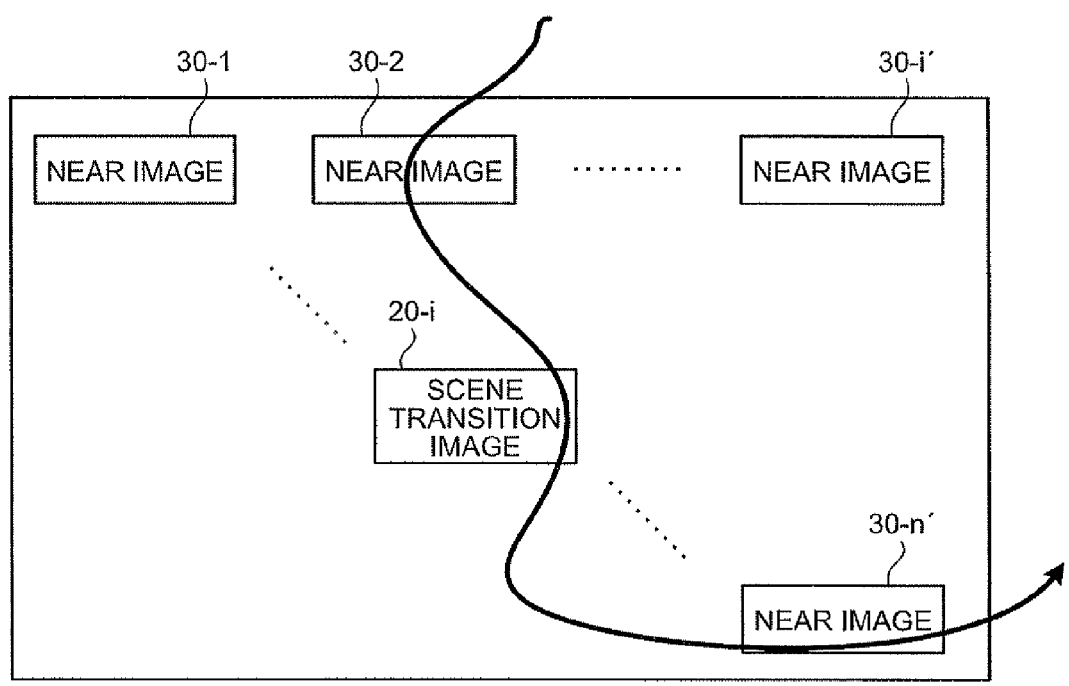
FIG. 11 is a diagram of a display example of images extracted by the image extracting apparatus shown in FIG. 1.

In the embodiment described above, the image for which the predetermined viewing operation is performed is an image for which the user performs the selection operation or the deletion operation. In a fifth modification, an image for which a pointing operation (clicking, for example) with a pointing device (pointer, for example) is performed as shown in FIG. 10, an image on which a movement trace of the pointing device passes, in other words, an image on which the pointer passes when viewed on the display screen 3*a* as shown in FIG. 11 are included in the image for which the predetermined viewing operation is performed.

An image extracting apparatus according to the fifth modification can use, on changing the extraction condition, information of an image which attracts attention of the user though the user does not positively perform the selection operation thereon, for example, an image on which the user clicks and an image over which the user passes the pointer. Thus, the extraction condition can be changed so as to reflect an intention of the user more extensively in comparison with the embodiment described above. Therefore, the scene transition image desired by the user can be more securely extracted.

Further, when the user can select a movie display or a thumbnail display, the image extracting apparatus may treat an image for which a command is issued for switching-over between the movie display and the thumbnail display as the image for which the predetermined viewing operation is performed.

Figure 12:
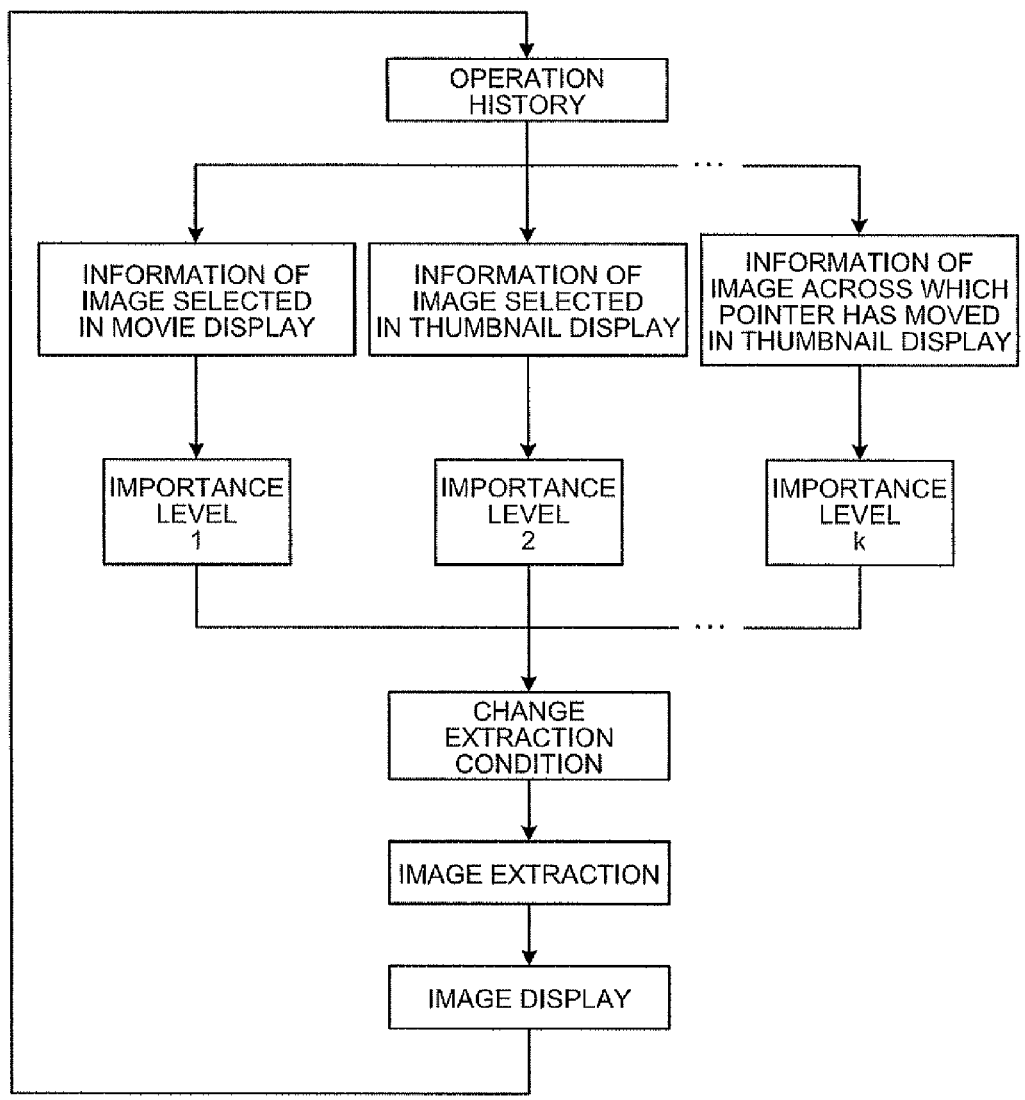
FIG. 12 is a schematic chart of a setting process of an importance level of image information.

In the embodiment described above, the extraction condition changing unit 15 determines whether an image for which the user performs an operation is an image desired by the user or not using history information of the operation, before changing the extraction condition using image information of each image. In a sixth modification, the image information is further weighted according to the content of operation the user performs, and employed for changing the extraction condition. As shown in FIG. 12, an image extracting apparatus according to the sixth modification sets an importance level of image information according to the operation the user performs and weights the image information of the image for which the predetermined operation is performed.

For example, for the image information of an image for which the user performs the selection operation while the image is displayed as a movie, the importance level is set to "1" meaning that it is most important information, whereas for the image information of an image on which the pointer passes while the image is displayed as a thumbnail, the importance level is set to "k" meaning that the information is not important though consideration should be paid. The weight of the image information of the image on which the pointer passes is set one third the weight of the image information of the image for which the user performs the selection operation. The extraction condition changing unit 15 assigns each value of a feature quantity variation matrix $F_i$, of an image for which the user performs the selection operation as it is, and one third of each value of a feature quantity variation matrix $F_i$, of the image on which the pointer passes, to the formula (6). Then, the extraction condition changing unit 15 calculates the weighting factor matrix w' of the feature quantity, that is, the extraction condition.

The image extracting apparatus according to the sixth modification estimates an importance level of each image for the user, using the history information of the operation, and changes the extraction condition using the image information weighted according to the importance level. Thus, an intention of the user can be reflected more accurately in changed extraction condition. Therefore, the scene transition image desired by the user can be more securely extracted.

Figure 13:
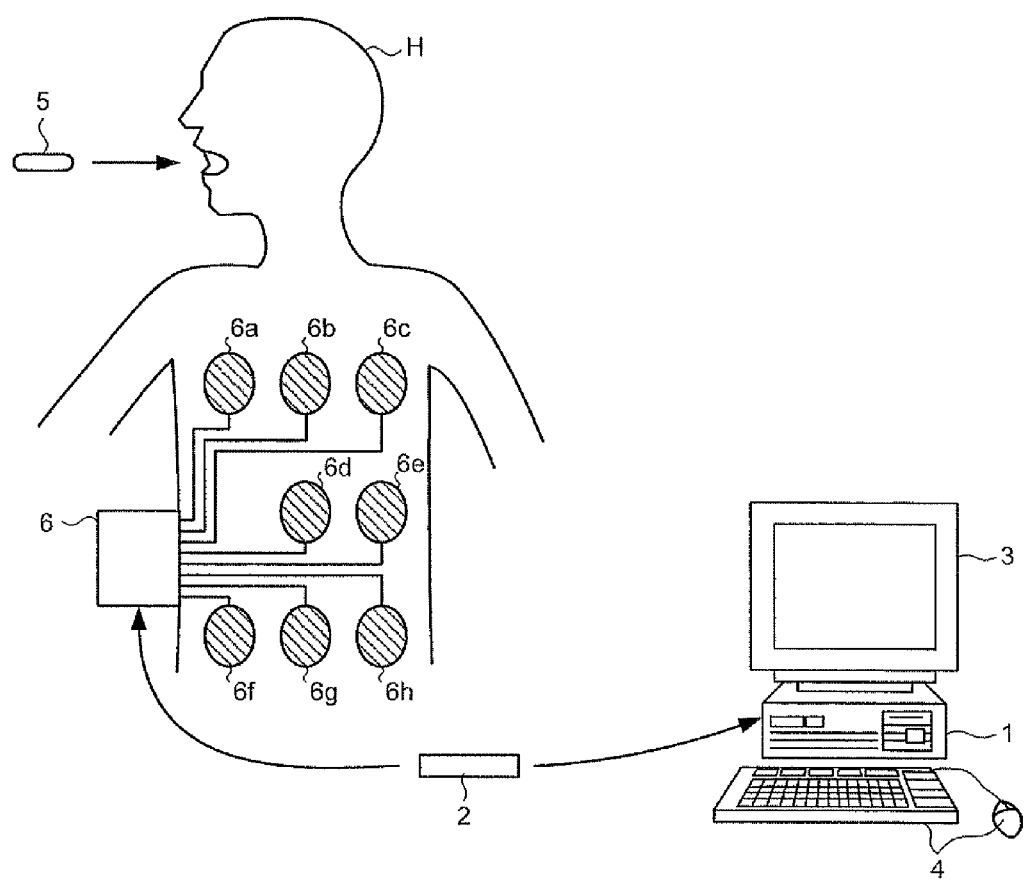
FIG. 13 is a schematic diagram of a configuration of an intra-subject information acquiring system according to an example of the present invention.

Next, one specific example of the image extracting apparatus according to the present invention is described. The image extracting apparatus according to the example of the present invention extracts an image from an image sequence (an intra-body-cavity image sequence) captured by a capsule endoscope. FIG. 13 is a schematic diagram of one example of an intra-subject information acquiring system provided with the image extracting apparatus of the example. The intra-subject information acquiring system shown in FIG. 13 has a capsule endoscope 5 that is introduced inside a body cavity of a subject H and captures an intra-body-cavity image, a receiving device 6 that receives a radio signal transmitted from the capsule endoscope 5 and stores an image included in the received radio signal, and the memory unit 2 such as a portable, removable memory card attachable to and detachable from the receiving device 6 and the image extracting apparatus.

The capsule endoscope 5 has an imaging function to capture an intra-body-cavity image of the subject H, and a radio communication function to transmit a radio signal including a captured image to an outside. To be more specific, the capsule endoscope 5 travels inside the body cavity of the subject H while capturing intra-body-cavity images at predetermined intervals, for example, at approximately 0.5-second intervals (i.e. about 2 Hz), and transmits the captured intra-body-cavity images on a predetermined radio wave to the receiving device 6.

The receiving device 6 is connected to receiving antennas 6a to 6h which receive a radio signal transmitted from the capsule endoscope 5. The receiving antennas 6a to 6h are realized, for example, with a loop antenna, and arranged in a scattering manner on a surface of the body of the subject H corresponding to a travel path of the capsule endoscope 5. As far as one or more receiving antenna is arranged for the subject H, a total number of arranged receiving antennas is not limited to eight as illustrated in the figure.

The receiving device 6 receives via one of the receiving antennas 6a to 6h the radio signal transmitted from the capsule endoscope 5, and acquires image information of the intra-body-cavity image of the subject H from the received radio signal. The image information acquired by the receiving device 6 is stored in the memory unit 2 attached to the receiving device 6. The memory unit 2 storing the image information of the intra-body-cavity image of the subject H is then attached to the image extracting apparatus and used for the process in the control unit.

In the intra-subject information acquiring system including each device described above, the capsule endoscope 5 travels inside the body cavity of the subject H for approximately eight hours while capturing an enormous amount of images, e.g., approximately 60000 image, and creates an intra-body-cavity image sequence. The intra-body-cavity image sequence, however, may contain many similar images, for example, in a scene captured while the capsule endoscope 5 is in the same internal organ, and thus it is not practical for a person to observe all images.

Against such a background, those in clinical practice who make diagnosis and perform treatment using the endoscope have been waiting for a technology which realizes accurate, short-time extraction of an image in which an object of interest such as a lesion appears. However, an object of interest in the intra-body-cavity image differs depending on medical departments, types of diseases, as well as individual doctors. Thus, it is difficult to develop an image extracting apparatus that allows extraction of any image desired by any doctor.

In the present example, the extraction condition of the scene transition image is changed so that an image in which a subject of interest of each doctor appears is extracted as the scene transition image from the intra-body-cavity image sequence of large amount captured by the capsule endoscope 5. Then, the scene transition image is re-extracted based on the extraction condition. To be specific, the extraction condition is changed according to the image information of an image selected from the scene transition images and near images by a doctor, and the history information of the operation by the doctor, and the scene transition image is re-extracted based on the changed extraction condition. Therefore, the doctor can easily search for a desired image and make diagnosis in a short time.

Figure 14:
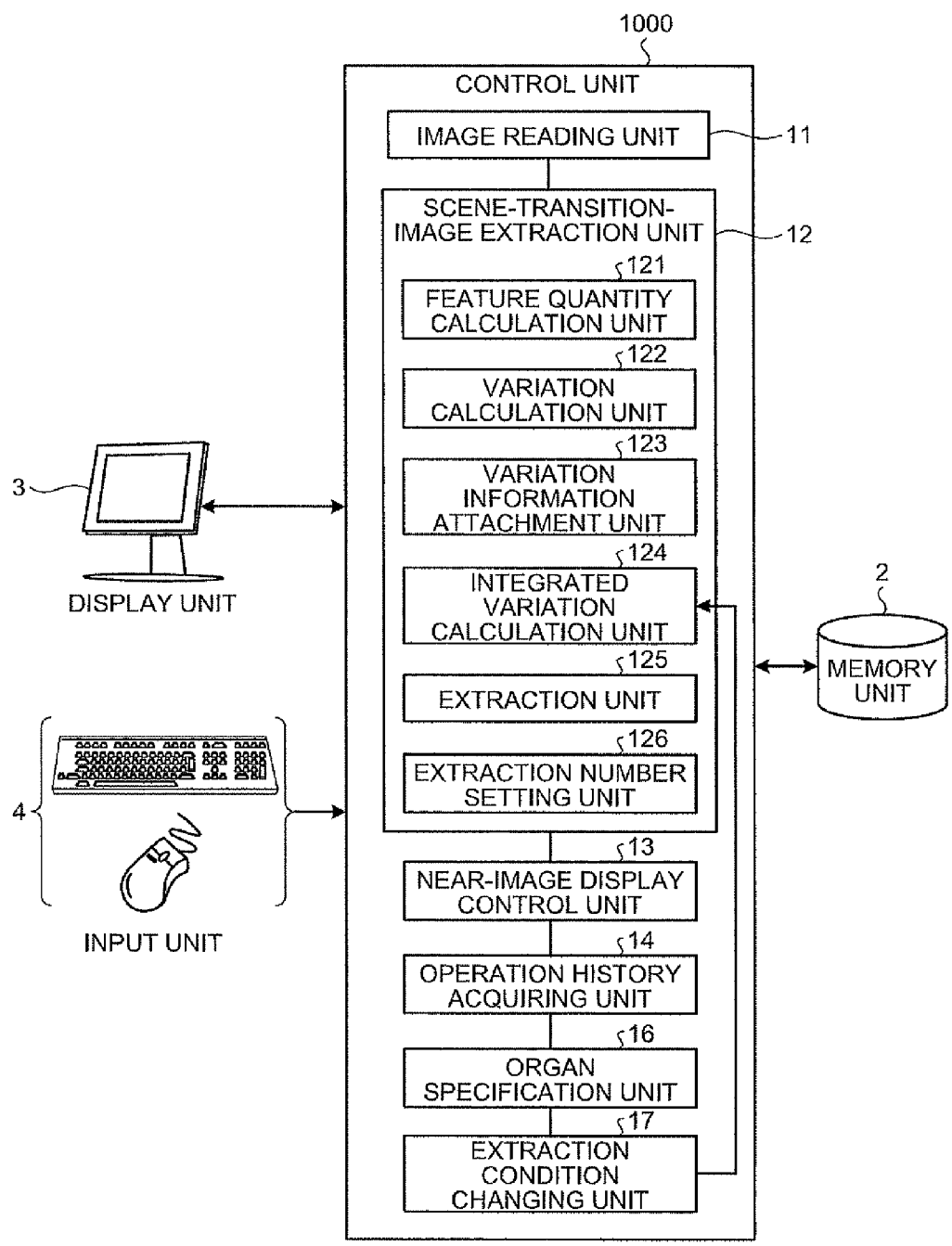
FIG. 14 is a block diagram of a configuration of an image extracting apparatus according to a modification of the example.

In a modification of the example described above, the image extracting apparatus included in the intra-subject information acquiring system according to the example further includes an organ specification unit 16 that specifies an organ appears in each image as shown in FIG. 14. The extraction condition of the scene transition image is changed for each organ which appears in the image. To be specific, information acquired by the operation history acquiring unit 14 is classified according to organs specified by the organ specification unit 16. The extraction condition changing unit 17 changes the extraction condition for each organ using the classified information. Thereafter, the scene-transition-image extraction unit 12 re-extracts the scene transition image changing the extraction condition for each organ appears in each image. As described above, the image extracting apparatus according to the modification of the example, which changes the extraction condition for each organ, allows for an even more secure extraction of the scene transition image desired by the doctor in comparison with the image extracting apparatus of the example.

The image extracting apparatus according to the embodiments is advantageous in that it allows for easy extraction of the scene transition image desired by the user.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image extracting apparatus, comprising:
a scene-transition-image extraction unit that extracts scene transition images from an image sequence captured in time series, using an extraction condition for extracting the scene transition images, each of the scene transition images being defined as an image where a transition of scene occurs;
a display unit that displays a plurality of images adjacent to one of the scene transition images and between a scene transition image right before the one of the scene transition images and a scene transition image right after the one of the scene transition images;
an operation history acquiring unit that acquires image information of an image for which a viewing operation is performed, among the plurality of images adjacent to the one of the scene transition images and history information of the viewing operation; and
a changing unit that changes the extraction condition using the image information and the history information of the viewing operation acquired by the operation history acquiring unit.

2. The image extracting apparatus according to claim 1, wherein
the display unit displays at least a number of images corresponding to a number of images captured during a time period between a time when a scene transition image in the scene transition images is captured and a time when another scene transition image in the scene transition images is captured.

3. The image extracting apparatus according to claim 1, wherein
the display unit displays at least half a number of images captured during a time period between a time when a scene transition image in the scene transition images is captured and a time when another scene transition image in the scene transition images is captured.

4. The image extracting apparatus according to claim 1, wherein
the display unit displays at least all images captured during a time period between a time when a scene transition image in the scene transition images is captured and a time when another scene transition image in the scene transition images is captured.

5. The image extracting apparatus according to claim 1, wherein
the display unit displays at least images captured previous to and subsequent to a time when a scene transition image in the scene transition images is captured.

6. The image extracting apparatus according to claim 1, wherein
the display unit sequentially displays the plurality of images in order of time series, and
the operation history acquiring unit acquires, when the plurality of images are sequentially displayed in order of time series by the display unit, the image information of one of the plurality of images for which one of a pausing operation, a frame advance forward operation, a frame advance backward operation, and a play backward operation is performed as the viewing operation, and the history information of the viewing operation.

7. The image extracting apparatus according to claim 1, further comprising
a pointing unit that points to the plurality of images displayed by the display unit, wherein
the operation history acquiring unit acquires the image information of one of the plurality of images for which a pointing operation by the pointing unit is performed as the viewing operation and history information of the viewing operation.

8. The image extracting apparatus according to claim 7, wherein
the operation history acquiring unit treats one of the plurality of images, on which a movement trace of the pointing unit passes, among the plurality of images displayed by the display unit, as the one of the plurality of images on which the viewing operation is performed, and acquires the image information of the one of the plurality of images and history information of the viewing operation.

9. The image extracting apparatus according to claim 7, wherein
the operation history acquiring unit acquires the image information of one of the plurality of images, which is displayed in a display mode by the display unit and for which an operation for displaying in a different display mode is performed as the viewing operation, among the plurality of images displayed by the display unit, and history information of the viewing operation.

10. The image extracting apparatus according to claim 1, wherein
the changing unit sets an importance level of the image information of one of the plurality of images, for which the viewing operation is performed, according to the viewing operation, and changes the extraction condition using the image information weighted according to the importance level.

11. The image extracting apparatus according to claim 1, further comprising
a number setting unit that sets a number of the images extracted by the scene-transition-image extraction unit.

12. The image extracting apparatus according to claim 1, further comprising
a feature quantity calculation unit that calculates various kinds of feature quantities for each of the images,
a variation calculation unit that calculates a variation of the feature quantity between images for each of the feature quantities, and
a variation attachment unit that attaches the variation calculated by the variation calculation unit to a corresponding one of the images, wherein
the scene-transition-image extraction unit calculates an integrated variation which is an integration of the variations of the feature quantities attached to each of the images, using a weighting factor that is set for each of the feature quantities as the extraction condition, and extracts an image in the image sequence using the integrated variation, and
the changing unit changes the weighting factor using the image information and the history information of the operation acquired by the operation history acquiring unit.

13. The image extracting apparatus according to claim 1, wherein
the image sequence is an intra-body-cavity image sequence captured by a capsule endoscope introduced inside a body cavity of a subject.

14. The image extracting apparatus according to claim 13, further comprising
an organ specification unit that specifies an organ where the image is captured, wherein
the changing unit changes the extraction condition for the organ specified by the organ specification unit, using the image information and the history information of the operation acquired by the operation history acquiring unit.

15. A computer program product having a computer readable recording device including programmed instructions, wherein the instructions, when executed by a computer, cause the computer perform:

extracting scene transition images from an image sequence captured in time series, using an extraction condition;

displaying a plurality of images adjacent to one of the scene transition images and between a scene transition image right before the one of the scene transition images and a scene transition image right after the one of the scene transition images;

acquiring image information of an image for which a viewing operation is performed, among the plurality of images adjacent to the one of the scene transition images and history information of the viewing operation; and changing the extraction condition using the image information and the history information of the viewing operation acquired in the acquiring.

16. An image extracting method comprising:

extracting scene transition images from an image sequence captured in time series, using an extraction condition;

displaying a plurality of images adjacent to one of the scene transition images and between a scene transition image right before the one of the scene transition images and a scene transition image right after the one of the scene transition images;

acquiring image information of an image for which a viewing operation is performed, among the plurality of images adjacent to the one of the scene transition images and history information of the viewing operation; and changing the extraction condition using the image information and the history information of the viewing operation acquired in the acquiring.

* * * * *